United States Patent [19]

Belanger et al.

[11] 4,424,355
[45] Jan. 3, 1984

[54] RESOLUTION OF SUBSTITUTED DIBENZO[b,f]THIEPIN-3-CARBOXYLIC ACID-5-OXIDES WITH BRUCINE OR EPHEDRINE

[75] Inventors: Patrice C. Belanger; Haydn W. R. Williams, both of Dollard des Ormeaux; Joshua Rokach, Chomeday-Laval, all of Canada

[73] Assignee: Merck & Co., Inc., Rahway, N.J.

[21] Appl. No.: 351,708

[22] Filed: Feb. 24, 1982

Related U.S. Application Data

[63] Continuation of Ser. No. 229,222, Jan. 28, 1981, abandoned.

[51] Int. Cl.³ .................. C07D 405/14; C07D 337/14
[52] U.S. Cl. ........................................ 546/35; 549/12
[58] Field of Search ............................ 549/12; 546/35

[56] References Cited

U.S. PATENT DOCUMENTS

| | | | |
|---|---|---|---|
| 2,390,281 | 12/1945 | Tishler et al. | 546/35 |
| 3,828,049 | 8/1974 | Karady et al. | |
| 4,104,280 | 8/1978 | Ackrell | 424/278 |
| 4,334,077 | 6/1982 | Belanger et al. | 549/12 |

Primary Examiner—Ethel G. Love
Attorney, Agent, or Firm—Ernest V. Linek; H. J. Pfeiffer

[57] ABSTRACT

The present invention is concerned with an improved process for the production of highly active optical isomers of (−) 7 or 8 fluorodibenzo[b,f]thiepin-3-carboxylic acid-5-oxide having the structural formula

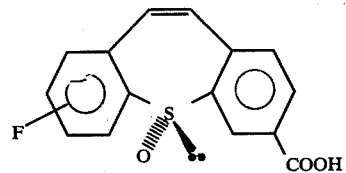

in which the fluoro substituent replaces a hydrogen in the 7 or 8 position. The two active isomers represented by formula II are S(−)7-fluorodibenzo[b,f]thiepin-3-carboxylic acid-5-oxide and R(−)8-fluorodibenzo[b,f]-thiepin-3-carboxylic acid-5-oxide. It is especially concerned with the resolution of the racemic 7 or 8 fluorodibenzo[b,f]thiepin-3-carboxylic acid-5-oxide by first forming and separating diastereomers of said racemic carboxylic acids by salt formation with brucine or ephedrine followed by crystallization and regeneration of the desired (−) isomers and recycling of the (+) isomer by racemization of the regenerated isomer. The compounds obtained in high yield by this process are highly active prostaglandin antagonists which are useful in treating a variety of conditions such as allergic asthma.

3 Claims, No Drawings

RESOLUTION OF SUBSTITUTED DIBENZO[B,F]THIEPIN-3-CARBOXYLIC ACID-5-OXIDES WITH BRUCINE OR EPHEDRINE

This is a continuation of application Ser. No. 229,222 filed Jan. 28, 1981, now abandoned.

BACKGROUND OF THE INVENTION

The compounds prepared by the process of the present invention are useful agents for the treatment of conditions such as allergic asthma because of their activity as prostaglandin antagonists. These compounds are disclosed to be present as components of a racemic mixture of compounds of the formula

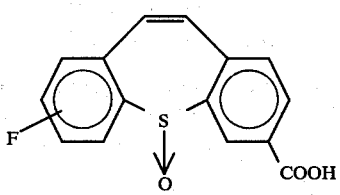

I 7 or 8 fluorodibenzo[b,f]thiepin-3-carboxylic acid-5-oxide. Both the 7 and 8 fluoro derivatives have unusually high prostaglandin antagonist activity and as disclosed in copending application U.S. Ser. No. 210,082 filed Nov. 24, 1980 of Rokach, Rooney and Cragoe the racemic mixtures can be resolved into (+) and (−) optical isomers in which the bioactivity resides exclusively in the (−) isomer. In the prior application the method of resolution disclosed involves formation of diastereoisomeric amide using an optically active amine, followed by tedious separation of diastereoisomers using fractional crystallization, chromatography and HPLC. In this manner, racemic 7 or 8 fluorodibenzo[b,f]thiepin-3-carboxylic acid-5-oxide of formula I is separated into the biologically active isomers of formula II and the corresponding biologically inactive compounds of formula III pictured structurally hereinbelow.

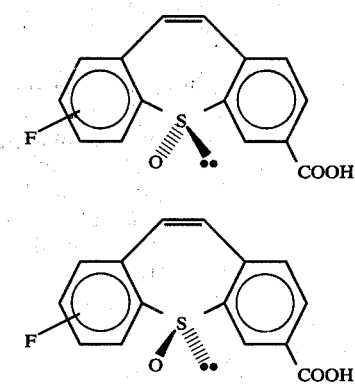

II

III

Formula II includes S(−)7-fluorodibenzo[b,f]thiepin-3-carboxylic acid-5-oxide and R(−)8-fluorodibenzo[b,f]-thiepin-3-carboxylic acid-5-oxide. Formula III includes R(+)7-fluorodibenzo[b,f]thiepin-3-carboxylic acid-5-oxide and S(+)8-fluorodibenzo[b,f]-thiepin-3-carboxylic acid-5-oxide.

DESCRIPTION OF THE INVENTION

This application is concerned with an improved process for the preparation of the (−)(7 or 8)fluoro-dibenzo[b,f]thiepin-3-carboxylic acid-5-oxides which employs the brucine and ephedrine diastereoisomeric salts of the racemic (7 or 8)fluoro-dibenzo[b,f]thiepin-3-carboxylic acid-5-oxide. This process is highly efficient because of the unique solubility properties of the diastereoisomeric salts and the ease of racemization of the (+) or biologically inactive form of the 5-oxide.

In one preferred embodiment of the improved process of resolution, the racemic (7 or 8)-fluoro-dibenzo[b,f]thiepin-3-carboxylic acid-5-oxide is treated in solution in acetonitrile with an equimolar amount of brucine (obtainable and usable as the dihydrate). Formation of the salt is insured by heating the mixtures until clear solution results. The solution is then allowed to stand for a period of 1–48 hours whereupon the brucine salt of the (+) or inactive form of the acid separates as a solid and is recovered by filtration. The inactive salt is readily hydrolyzed by treatment with aqueous acid to produce the inactive acid followed by racemization by treatment with trifluoroacetic anhydride which is recycled as starting material. The (−) or active form of the acid is readily recovered by evaporation of the filtrate to dryness to yield the brucine salt of the predominantly (−) or active form of the acid having an enantiomeric purity of 70% or better. The brucine salt prepared in this manner is hydrolyzed in aqueous acid and the partially purified acid readily purified by recrystallization for example from acetic acid to yield substantially pure (−)(7 or 8)fluoro-dibenzo[b,f]-thiepin-3-carboxylic acid-5-oxide.

The process is outlined in the following flow sheet as applied to the 8-fluoro isomer.

FLOW SHEET

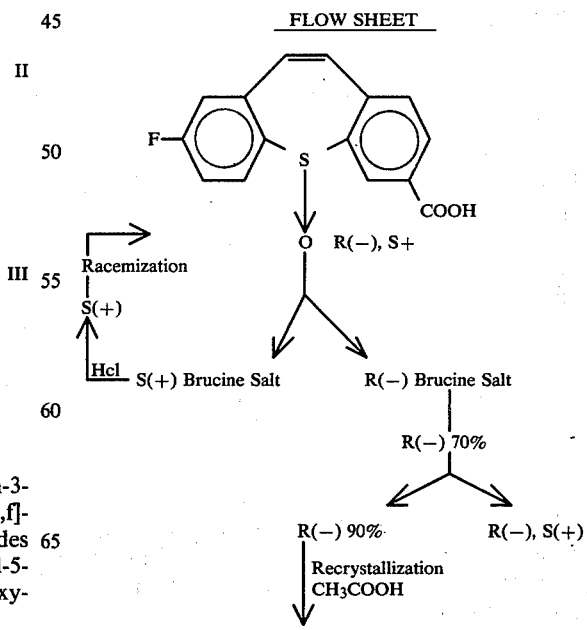

-continued
FLOW SHEET

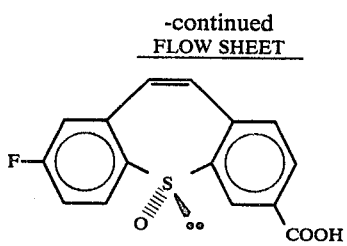

The process is applicable in the same manner for the preparation of the corresponding S(−)7-fluorodibenzo[b,f]thiepin-3-carboxylic acid-5-oxide.

In a second preferred embodiment of the improved process of resolution, the racemic (7 or 8) fluoro-dibenzo[b,f]thiepin-3-carboxylic acid-5-oxide is added in equivalent quantity to a solution of l-ephedrine in a lower alcohol preferably ethanol and the solution is heated until all solids are dissolved. The ephedrine salt of the (−) (7 or 8) fluoro-dibenzo[b,f]thiepin-3-carboxylic acid-5-oxide crystallizes from solution in substantially pure form. Further purification may be achieved by recrystallization from methanol. The (−) or bioactive form of the acid is obtained by treatment of the purified ephedrine salt with aqueous acid which regenerates and precipitates the relatively pure enantiomer (−) (7 or 8)fluorodibenzo[b,f]thiepin-3-carboxylic acid-5-oxide. The inactive enantiomer which is present in the mother liquors of the above crystallization is readily converted to the racemic acid by first treating with aqueous acid to hydrolyze the salt and form the (+) (7 or 8)fluorodibenzo[b,f]-thiepin-3-carboxylic acid-5-oxide followed by racemization by treatment with trifluoroacetic anhydride. The racemic acid is recycled into the process as illustrated in the following flow sheet for the 8-fluoro isomer.

Crystallization of the ephedrine salt:

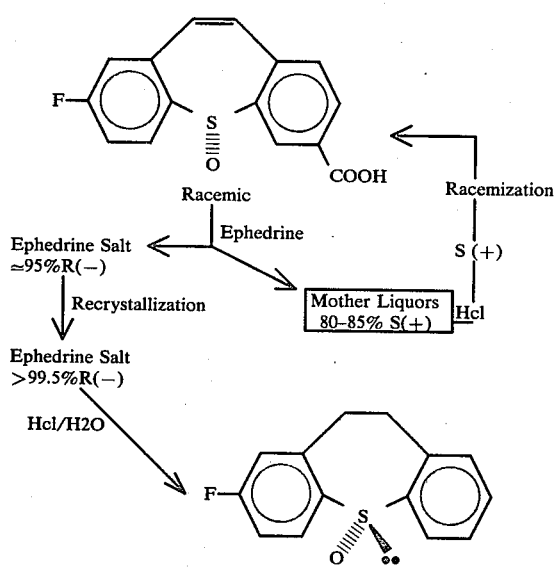

The process is applicable in the same manner starting with racemic 7-fluorodibenzo[b,f]thiepin-3-carboxylic acid-5-oxide to produce the desired S(−)7-fluorodibenzo[b,f]thiepin-3-carboxylic acid-5-oxide.

EXAMPLE 1

Step A. Brucine Salt of S(+)8-fluorodibenzo[b,f]-thiepin-3-carboxylic Acid

In a 22 liter flask is introduced acetonitrile (15 liters) and racemic acid 8-fluorodibenzo-[b,f]thiepin-3-carboxylic acid-5-oxide (216 g.; 0.75 mole). The suspension is brought to reflux. Brucine dihydrate (315 g., 0.79 mole) is then added. Heating is continued until complete dissolution is obtained. The solution is then left at room temperature for a period of two days and stirring is maintained during this period. The salt of the S(+)acid is filtered, washed with a small volume of acetonitrile, and air dried. The yield is 162 g. (30%).

The mother liquors are evaporated to dryness to yield a residue which is enriched in the R(−)acid.

HPLC analysis of the salt indicates it is 92% S-isomer whereas the mother liquors are 72% R-isomer.

HPLC ANALYSIS

The HPLC analysis is based on the separation of the diastereoisomers formed when the sulfoxide acid is reacted with optically active α-methyl benzylamine.

The procedure is as follows:

1-2 mg. of sulfoxide acid derivative to be analyzed is dissolved in 0.3 ml THF. To this is added 2-3 drops of triethylamine. After stirring for a few seconds, ethyl chloroformate (2-3 drops) is added. Stirring is maintained for a few seconds; l-(−)-α-methylbenzylamine (2-3 drops) is then added. The mixture can then be analyzed by HPLC on a μ-Porasil column, using as eluent a 7:3 mixture of chloroform:heptane. Under these conditions, the amide of the R-isomer of the 8-fluoro compound is the most polar of the two diastereoisomers.

Step B. R(−)8-Fluorodibenzo[b,f]Thiepin-3-Carboxylic Acid-5-Oxide

The residue obtained by evaporating the mother liquors from part 1A to dryness (72% R; 352 g.) is dissolved in tetrahydrofuran (2 liters) and the resulting solution is added slowly in a stirred 3 N hydrochloric acid solution. After stirring for an additional 10 minutes, the insolubles are filtered, washed successively with 1 N hydrochloric acid, and with water. It is then air dried to yield 72% R(−)8-fluorodibenzo[b,f]thiepin-3-carboxylic acid-5-oxide (148 g.).

The free acid is recrystallized from acetic acid (3 liters). After 7 hours at room temperature, the solid is filtered and washed with a small volume of acetic acid. This acid (64.3 g.) is found to be racemic acid by HPLC analysis. The filtrate is evaporated to a small volume, water (1 liter) is added and the insolubles are filtered, washed with water until neutral, and air dried. The acid isolated at this point is 92% by HPLC.

Recrystallization from acetic acid (12 ml. per gram) raises the enantiomeric purity to better than 99% R. The yield of acid is 39.5 g. (18%).

M.P. 263°-267° C. (dec.), resolidifies and remelts at 327° C. Optical rotation: −26.8° (C=1 in THF).

Step C. Racemization Of The S-Acid

The S-acid obtained as described in Example 1A is added slowly with stirring to trifluoroacetic anhydride (1.35 liter). The reaction is started by heating gently with a heat gun. After the addition, the mixture is allowed to stand at room temperature for an additional two hours. It is then poured on ice (−10 Kg.), the insolubles are filtered and washed with water. After drying, the recovered acid (453 g.: 98.7%) is found to be racemic by measuring the optical rotation. HPLC analysis also showed the product to be racemic.

EXAMPLE 2

S(−) 7-Fluorodibenzo[b,f]Thiepin-3-Carboxylic Acid-5 Oxide

The procedure of Example 1A, B and C is repeated using racemic acid 7-fluorodibenzo[b,f]-thiepin-3-carboxylic acid-5-oxide as the starting material in place of the corresponding 8-fluoro compound. In this instance the brucine salt of the R(+) 7-fluorodibenzo[b,f]thiepin-3-carboxylic acid-5-oxide is precipitated from solution and the S(−)7-fluorodibenzo[b,f]thiepin-3-carboxylic acid is isolated from the mother liquors. As in the previous instances, the precipitated brucine salt is racemized and recycled.

EXAMPLE 3

Improved Process Using Ephedrine Salt Method

Step A. Crystallization of the Ephedrine Salt of R(−)-8-Fluorodibenzo[b,f]Thiepin-3-Carboxylic Acid-5-Oxide In a 5 liter flask containing ethanol (3.4 liters) is introduced l-ephedrine (143.2 g.; 0.868 mole). Racemic 8-fluorodibenzo[b,f]thiepin-3-carboxylic acid-5-oxide (250 g.; 0.868 mole) is added rapidly to this solution and brought to reflux. After the addition, the reflux is continued until complete solution is obtained. The resulting solution is then left at room temperature overnight. The crystals are filtered, washed with a small volume of ethanol and air dried to yield the ephedrine salt of the title product having an enantiomeric purity of 93% (134.2 g.; 68%).

Recrystallization from methanol (10 ml. per gram) raises the enantiomeric purity to better than 99% R(−) in a yield of 85%. This salt melts at 211°–213° C. and has an optical rotation of −63±1° (C=1 in methanol).

R(−)-fluorodibenzo[b,f]thiepin-3-carboxylic acid-5-oxide is regenerated from the ephedrine salt by treating with dilute HCl in methanol:water 9:1 9v:v). It is found to be identical to the product obtained from the brucine salt.

$[\alpha]_D^{25} = -27.7°$ (C=1 in THF).

Step B. Racemization of S(+) 8-Fluorodibenzo[b,f]-Thiepin-3-Carboxylic Acid-5-Oxide The mother liquors from the above crystallization, which are predominantly the ephedrine salt of the S(+) acid are acidified and treated with trifluoroacetic anhydride as described in Example 1C to produce the racemic acid.

The procedure of Example 3 is repeated using the racemic 7-fluorodibenzo[b,f]thiepin-3-carboxylic acid-5-oxide as the starting material in place of the corresponding 8-fluoro compound. In this instance, the ephedrine salt of the active S(−) 7-fluorodibenzo[b,f]thiepin-3-carboxylic acid-5-oxide is crystallized directly from the reactive mixture in high yield and the inactive R(+) 7-fluorodibenzo[b,f]thiepin-3-carboxylic acid-5-oxide is recovered from the filtrate and reconverted to racemic acid for recycling.

What is claimed is:

1. An improved process for the preparation of (−) 7 or (−) 8-fluoro-dibenzo[b,f]thiepin-3-carboxylic acid-5-oxide of the formula I, having an enantiomeric purity of at least 70 percent,

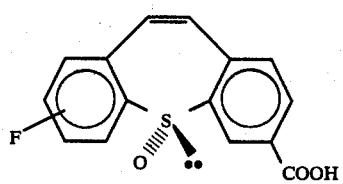

which comprises:
(1) Heating the racemic sulfoxide acid, (7 or 8)-fluorodibenzo[b,f]thiepin-3-carboxylic acid-5-oxide with an equimolar amount of brucine to form a diastereoisomeric mixture of brucine salts of the corresponding (−) and (+) acids;
(2) Recycling the major portion of the brucine (+) acid salt by crystallization, acidification and racemization to regenerate the starting racemic sulfoxide acid;
(3) Recovering the brucine (−) acid salt by evaporation of the crystallization mother liquors;
(4) Acidifying said brucine (−) acid salt to produce the desired sulfoxide acid product and recovering said product by crystallization.

2. The brucine salt of (−) 7 or 8 fluorodibenzo[b,f]thiepin-3-carboxylic acid-5-oxide.

3. The brucine salt of (+) 7 or 8-fluorodibenzo[b,f]thiepin-3-carboxylic acid-5-oxide.

* * * * *